United States Patent [19]

Schlesser et al.

[11] Patent Number: 4,643,725
[45] Date of Patent: Feb. 17, 1987

[54] COMBINATION PACKAGE AND APPLICATOR

[76] Inventors: Marilyn Schlesser, 42-11 NE. 23 Terr., Lighthouse Point, Fla. 33064; Marie Bernard, 6451 Park View Dr., Boca Raton, Fla. 33433

[21] Appl. No.: 750,020

[22] Filed: Jul. 1, 1985

[51] Int. Cl.$^4$ ............................................. A61F 13/00
[52] U.S. Cl. ................................................ 604/306
[58] Field of Search ................................ 604/304–310, 604/289, 3, 365, 290; 401/126–132

[56] References Cited

U.S. PATENT DOCUMENTS

| | | | |
|---|---|---|---|
| 3,363,625 | 1/1968 | Jovis | 604/289 |
| 4,140,409 | 2/1979 | DeVries | 604/289 X |
| 4,252,119 | 2/1981 | Coates | 604/306 |
| 4,281,650 | 8/1981 | Spiegelberg | 604/365 |
| 4,360,020 | 11/1982 | Hitchcock, Jr. et al. | 604/289 |

FOREIGN PATENT DOCUMENTS 2834801  2/1980  Fed. Rep. of Germany ...... 604/289

*Primary Examiner*—John D. Yasko
*Attorney, Agent, or Firm*—Steinberg & Raskin

[57] ABSTRACT

A combination package and applicator for a greasy and/or moist substance to be applied to the body or other articles includes a substance impregnated carrier pad firmly attached to an impermeable backing sheet. The package is closed either laminating a cover sheet of impermeable material over the carrier pad to form a sandwich-type package or by folding the backing sheet so that the carrier pad is located between opposed regions of the backing sheet and sealing the opposed edge regions of the backing sheet to each other. A grasping handle is provided by which the user can grasp the backing sheet after the package has been opened and apply the substance without the fingers coming into contact with the substance.

9 Claims, 10 Drawing Figures

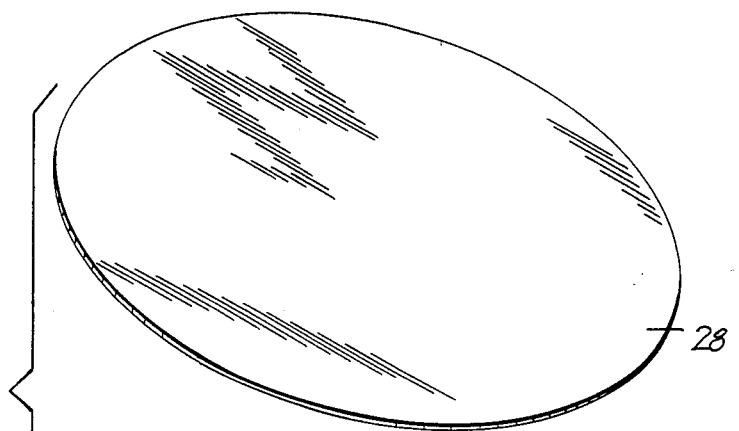
FIG. 5
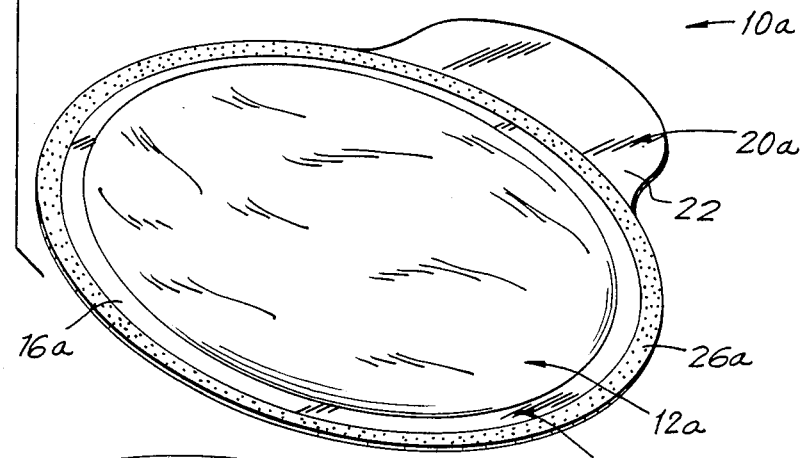
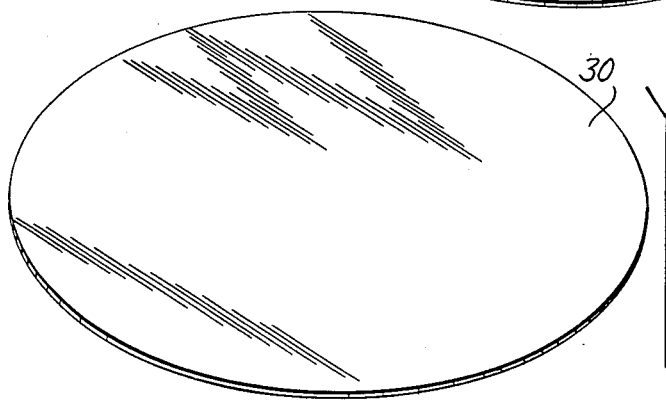
FIG. 6
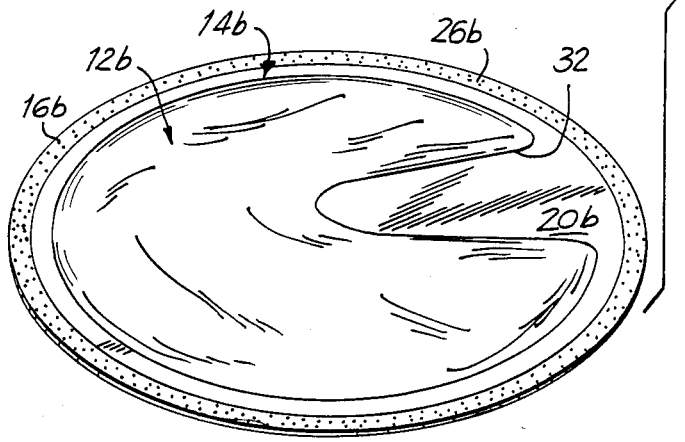

COMBINATION PACKAGE AND APPLICATOR

BACKGROUND OF THE INVENTION

This invention relates generally to the packaging of moist or greasy substances intended for application to the body and other articles and to the application of such substances.

Generally, moist and/or greasy substances intended for application to the body and other articles, such as tanning oil, cosmetic and nail polish remover, shoe polish and the like, are packaged in bottles or tubes. Such substances are dispensed either directly onto the body or articles and spread over the desired body or articles region by hand or onto a cotton or gauze pad or like applicator which is then rubbed on the body or article by hand. In either case, the substance must then be wiped or washed from the user's hand. In the case where the substance is to be applied when the user is at a remote location, it is often inconvenient for the user to carry the bottle or tube containing the substance with him. For example, a sun bather at the beach may forget to take his or her bottle of tanning oil or lotion. Moreover, small amounts of the tanning lotion may spill onto the outer surface of the bottle requiring that the bottle be kept separate from other articles carried by the user. Of course, the user's hands become oily or greasy from application of the tanning substance to the body.

It would therefore be desirable to provide a package for moist and greasy substances to be applied to the body or other articles which also functions as an applicator for the substance in a manner such that the substance only comes into contact with the region of the body or article to which application is desired and will not, for example, contact the hands of the user during application.

SUMMARY OF THE INVENTION

Accordingly, it is an object of the present invention to provide a new and improved package for greasy and/or moist substances intended for application to the body or other articles which also functions as an applicator for the substance.

Another object of the present invention is to provide a new and improved combination package and applicator for greasy and/or moist substances wherein the substance comes only into contact with the regions of the body or article to which application is desired during application of the substance.

Still another object of the present invention is to provide a new and improved combination package and applicator for greasy and/or moist substances which is disposable after a single application.

Briefly, in accordance with the present invention, these and other objects are attained by providing a combination package and applicator comprising a carrier, such as an absorbent fibrous pad, impregnated with the moist and/or greasy substance. The impregnated carrier is firmly and substantially permanently attached to the inner surface of a backing sheet of material which is impermeable to moisture and grease, such as metallic foil or the like. The package is formed either by laminating a cover sheet of impermeable material over the carrier and sealing the backing and cover sheets to each other around the carrier to form a sandwich-type package or by folding the backing sheet so that the carrier is located between opposed regions of the backing sheet and then sealing opposed edge regions of the backing sheet to each other. Grasping means are provided by which the user can grasp the backing sheet after the package has been opened without coming into contact with the substance impregnated carrier. In one embodiment the grasping means comprises a handle formed of an elongated flexible member having ends affixed to the outer surface of the backing sheet. In other embodiments, the grasping means are formed by appropriately shaping the carrier and/or the backing sheet in a manner such that a free region of the backing sheet is provided which can be firmly grasped in the manner of a handle so that the substance impregnated carrier can be rubbed against the body to apply the substance thereto. In another embodiment, the grasping means are formed by constructing the backing sheet as a glove-like member into which the user's hand can be inserted.

DETAILED DESCRIPTION OF THE DRAWINGS

A more complete appreciation of the present invention and many of the attendant advantages thereof will be readily understood by reference to the following detailed description when considered in connection with the accompanying drawings in which:

FIG. 5 is an exploded perspective view of a second embodiment of a combination package and applicator in accordance with the present invention;

FIG. 6 is an exploded perspective view of a third embodiment of a combination package and applicator in accordance with the present invention;

DESCRIPTION OF THE PREFERRED EMBODIMENTS

Figure 1:
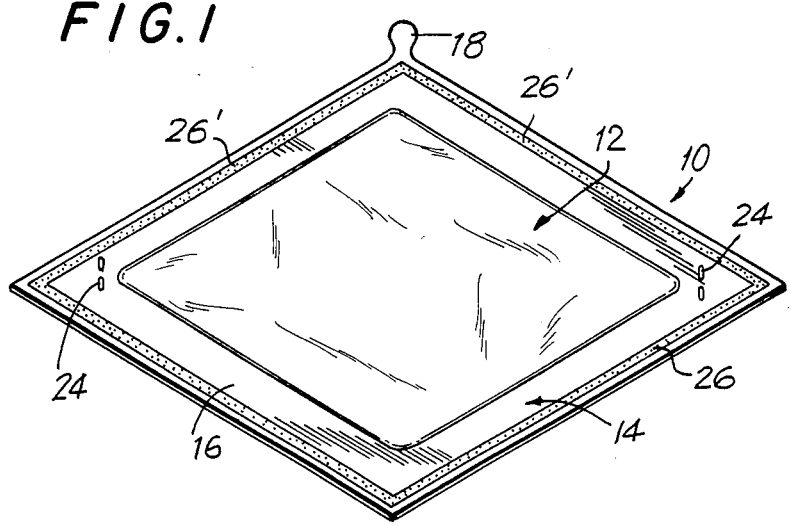
FIG. 1 is a top perspective view of one embodiment of a combination package and applicator in its open configuration in accordance with the present invention.

Although the present invention is described herinbelow as applied to a combination package and applicator for tanning oil, it will be understood that the invention is equally applicable to other moist and/or greasy substances intended to be applied to the body or various articles, such as medicines, polishes and the like.

Referring now to the drawings wherein like reference characters designate identical or corresponding parts throughout the several views, and more particularly to the embodiment of the invention illustrated in FIGS. 1-4, a combination package and applicator, generally designated 10, comprises a carrier in the form of an absorbent fibrous pad 12. The pad 12 is impregnated with tanning oil so as to be substantially saturated therewith. The pad 12 is substantially permanently attached to the inner surface of a flexible backing sheet 14 formed of a material that is impermeable to moisture and grease, such as aluminum foil appropriately prepared paper or the like. Any suitable means can be used to attach the pad 12 to the backing sheet 14 including adhesives and mechanical fasteners, such as staples.

In the illustrated embodiment, the pad 12 and backing sheet 14 are both substantially square with the pad 12 being somewhat smaller than the backing sheet 14 to thereby define a narrow peripheral region 16 of the backing sheet 14 bordering the pad 12. A tab 18 is formed at one corner of the backing sheet 14.

Figure 2:
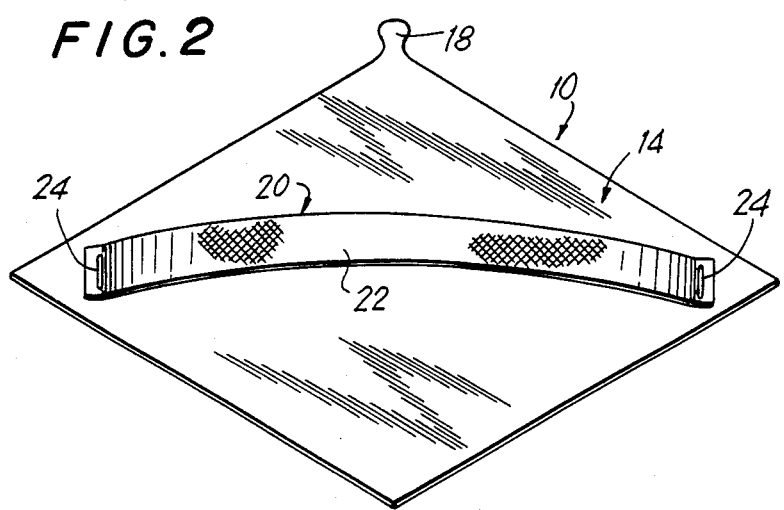
FIG. 2 is a bottom perspective view of the combination package and applicator shown in FIG. 1.

Referring to FIG. 2, grasping means are provided in the form of a handle 20. Handle 20 comprises a strip 22 of elongate flexible material, such as plastic, elastic fabric or paper, whose ends are affixed to opposed corner regions of the outer surface of the backing sheet 14, such as by staples 24, adhesive or the like.

In the assembly of the closed combination package and applicator 10, the backing sheet 14 is folded by bringing its corner opposite from the corner at which tab 18 is formed to the latter with the sheet inner surface and pad 12 on the inside and securing the fold portions to each other by means of a suitable adhesive 26 which is applied to the inner surface of the peripheral region 16 in a continuous circumferential strip, preferably spaced somewhat inwardly from the outer edge of the backing sheet. The adhesive can be one that is actuated by heat and pressure and which will allow the fold portions to be peeled from each other to open the package. It will be recognized that it is not necessary to provide the adhesive 26 around the entire circumference. Thus, it is sufficient if the adhesive is applied only on two adjacent sides of a single fold portion, such as 26'. The flexible strip 22 of handle 20 has sufficient slack to allow the folding described above as best seen in FIGS. 3 and 4.

Figure 4:
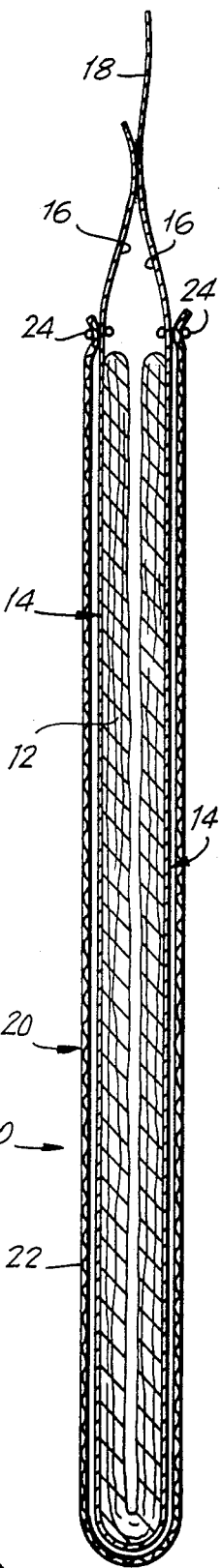
FIG. 4 is a section view taken along line 4—4 of FIG. 3.
Figure 3:
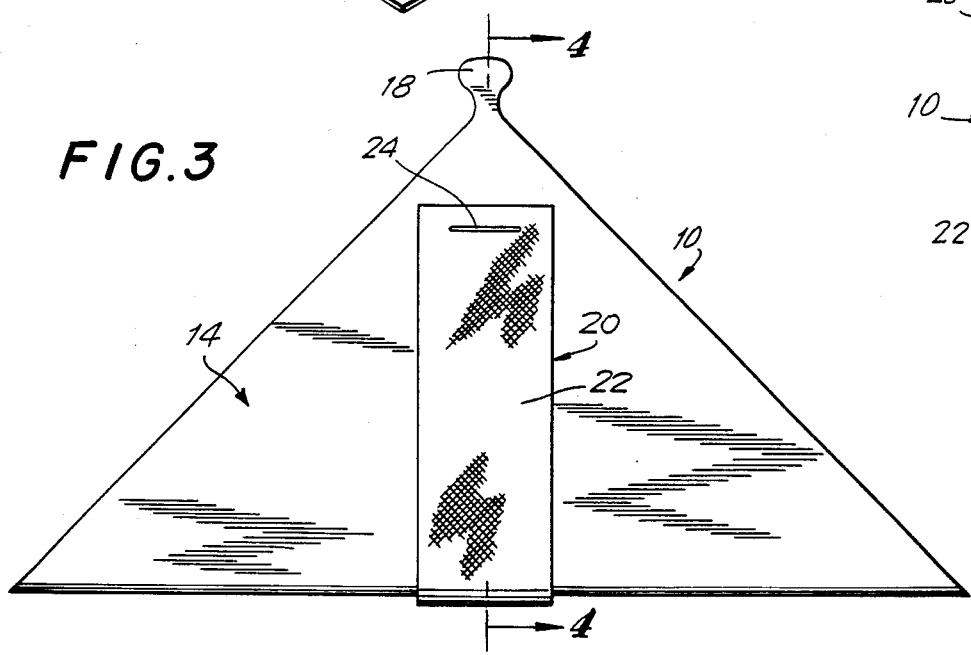
FIG. 3 is a front elevation view of the combination package and applicator shown in FIG. 1 but in its closed configuration.

Referring to FIGS. 3 and 4, when the user desires to apply the tanning oil, the combination package and applicator is held in one hand by the tab 18 and the thin edge of the opposed fold portion of the backing sheet 14 situated outwardly of adhesive 26 is gripped by the other hand whereupon the fold portions are peeled apart to expose the pad 12 impregnated with tanning oil. The combination package and applicator 10 is then grasped by handle 20 and the tanning oil applied by rubbing the impregnated pad over the regions of the body to which it is desired to apply the oil. It is apparent that the user's hands will not ever contact the tanning oil during its application. When application has been completed, the combination package and applicator is discarded.

The embodiment of the invention described above and shown in FIGS. 1-4 is also advantageous in that the combination package and applicator can maintain the substance-impregnated pad in a sealed condition using only a single sheet of moisture and grease impermeable material thereby reducing the costs of manufacture.

Second, third, fourth and fifth embodiments of a combination package and applicator in accordance with the invention are illustrated in FIGS. 5, 6, 7 and 8-10 respectively. Elements corresponding to those of the embodiment of FIGS. 1-4 will be designated by the same reference numerals with the suffixes "a", "b", "c" and "d" respectively.

Referring to FIG. 5, a combination package and applicator 10a comprises a carrier pad 12a impregnated with tanning oil substantially permanently attached to the inner surface of a flexible impermeable backing sheet 14a. The pad 12a and backing sheet 14a have substantially rounded configurations with a peripheral region 16a of the backing sheet 14a bordering the pad 12a. A continuous strip of adhesive 26a is applied to the inner surface of the peripheral region 16a to surround the pad 12a.

Grasping means are provided in the form of a handle 20a. Handle 20a comprises an integral extension 22a of the backing sheet 14a which extends outwardly beyond the adhesive strip 26a to an extent such that it can be firmly grasped. In assembly of the closed combination package and applicator 10a, a separate cover sheet 28 of impermeable flexible material, such as aluminum foil, is provided over the pad 12a and sealed to the backing sheet 14a to form a sandwich type package containing the carrier 12a. The cover sheet 28 extends radially beyond the outer edge of the adhesive strip 26a to allow it to be gripped to facilitate opening the package.

When the user desires to apply the tanning oil, the combination package and applicator is held in one hand by handle 20a whereupon the cover sheet 28 is peeled from the backing sheet 14a to expose the impregnated pad 12a. Still grasping the combination package and applicator 10a by handle 20a, the tanning oil is applied by rubbing the impregnated pad over the regions of the body to which it is desired to apply the oil. The user's hand will not come into contact with the tanning oil during its application.

The embodiment of the invention described above and shown in FIG. 5 is also advantageous in that the handle 20a is formed integrally with the backing sheet 14a thereby simplifying its manufacture and reducing costs.

Referring to FIG. 6, a combination package and applicator 10b in accordance with the invention is shown which is similar to the embodiment shown in FIG. 5. The closed combination package and applicator 10b is formed by the backing sheet 14b to which the pad 12b is permanently affixed and a cover sheet 30 sealed to the backing sheet by adhesive 26b. The combination package and applicator 10b differs from that shown in FIG. 5 with respect to the grasping means. As seen in FIG. 6, the pad 12b is formed with a finger-receiving recess 32 which exposes a relatively wide area 20b of the inner surface of backing sheet 14b. The exposed area 20b enables that portion of the backing sheet to function as a handle during the application of the tanning oil to the body as will be readily apparent. Thus, after opening the combination package and applicator 10b as described above in connection with the embodiment of FIG. 5, the backing sheet can be firmly grasped by handle area 20b without the fingers coming into contact with the tanning oil during application.

Figure 7:
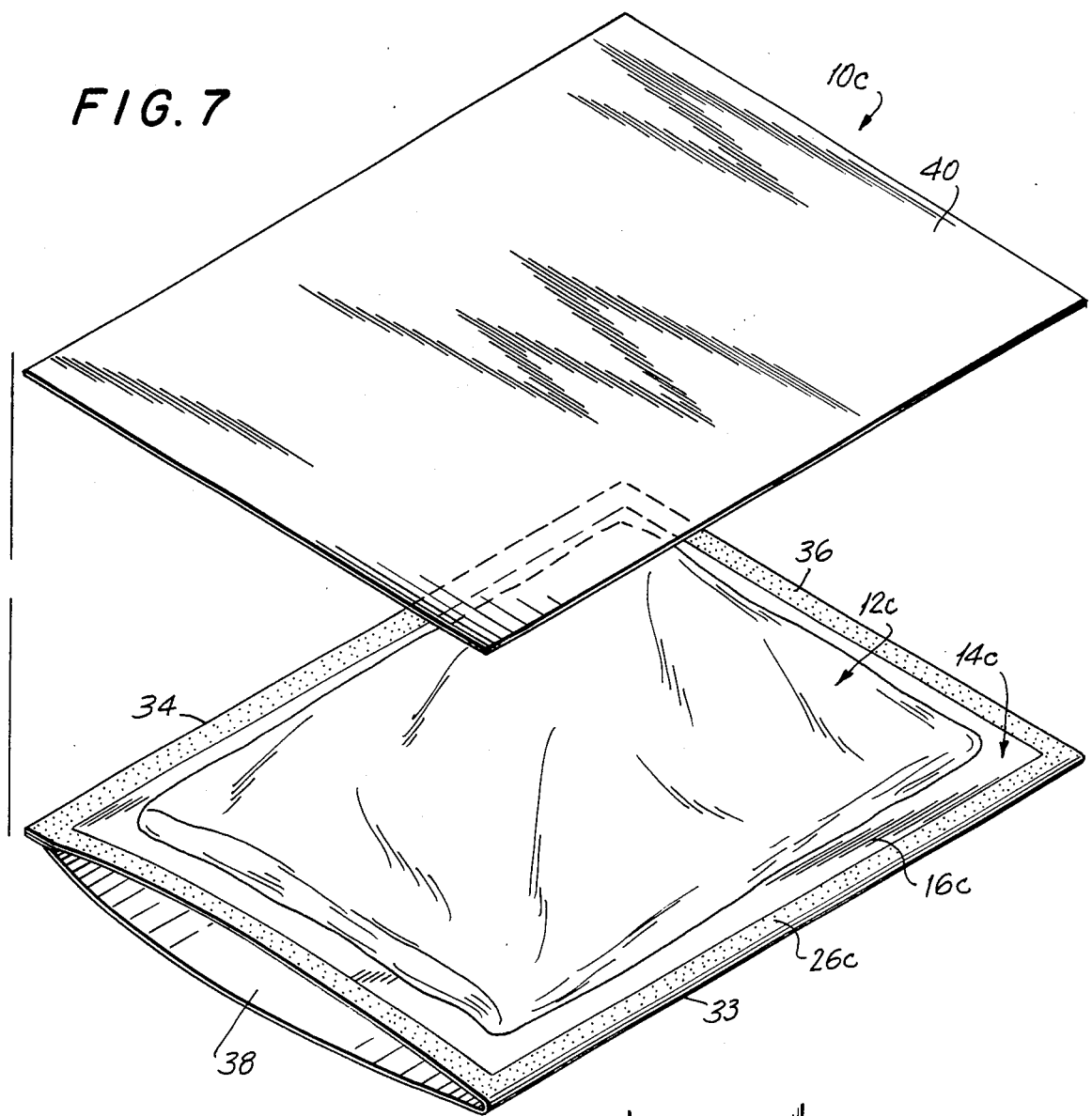
FIG. 7 is an exploded perspective view of a fourth embodiment of a combination package and applicator in accordance with the present invention.

Referring to FIG. 7, a combination package and applicator 10c comprises a carrier pad 12c impregnated with tanning oil substantially permanently attached to the inner surface of a flexible impermeable backing member 14c. The pad 12c and backing member 14c have substantially rectangular configurations with a peripheral region 16c of the backing member 14c bordering the pad 12c.

Grasping means are provided by forming the backing member 14c as a mitt-like member into which the user's hand can be inserted. In particular, the backing member 14c is formed from a flexible sheet which is folded over itself at a fold line 33 with opposed fold portions glued to each other along regions 34 and 36 to form a mitt-like member having an open end 38 through which at least several fingers of the user's hand can be inserted.

In assembly of the closed combination package and applicator 10c, a separate cover sheet 40 of impermeable material is provided over the pad 12c and sealed to the backing member 14c along peripheral region 16c by means of adhesive 26c.

In use, the cover sheet 40 is peeled from the backing member 14c to expose the impregnated pad 12c. The user inserts his hand into the interior of the mitt-like backing member and applies the tanning oil. It is seen that the user's hand will not come into contact with the tanning oil during its application.

Figure 10:
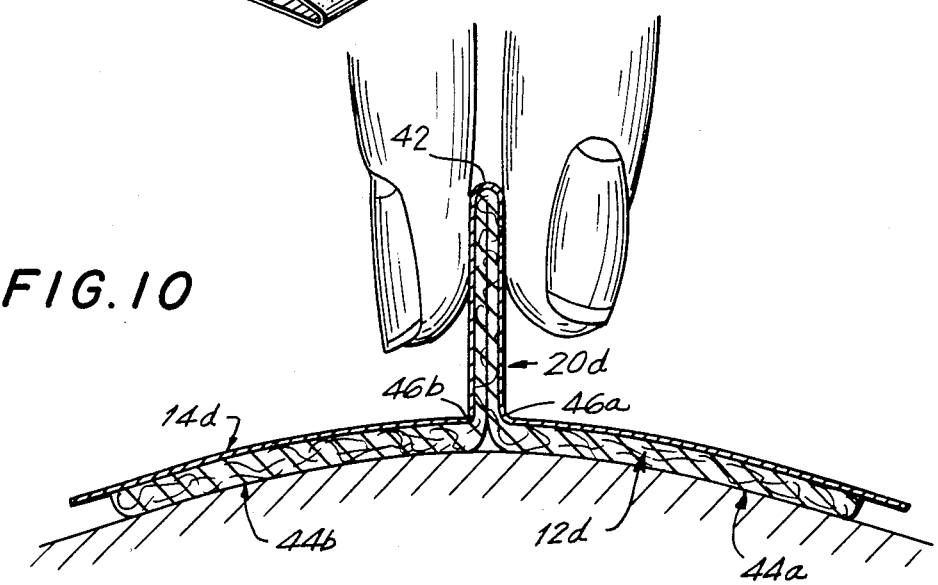
FIG. 10 is a side sectional view of the combination package and applicator of FIGS. 8 and 9 during use.
Figure 8:
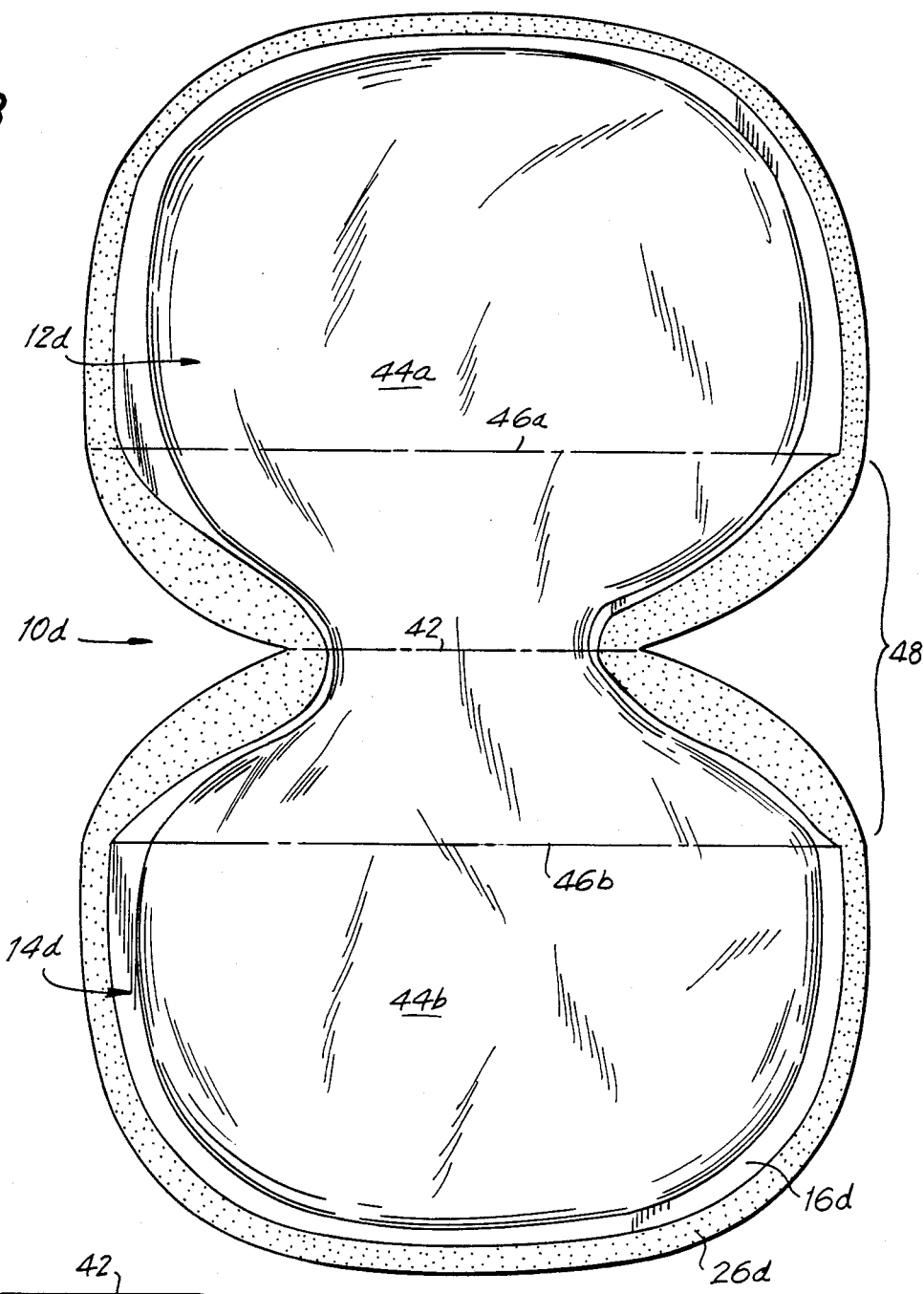
FIG. 8 is a top plan view of a fifth embodiment of a combination package and applicator in accordance with the present invention in its open configuration.
Figure 9:
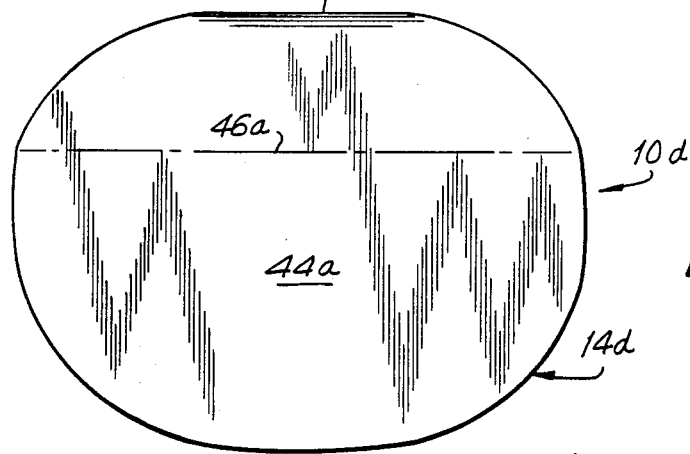
FIG. 9 is a plan view of the combination package and applicator of FIG. 8 in its closed configuration.

Referring to FIGS. 8-10, another embodiment of a combination package and applicator 10d comprises a carrier pad 12d impregnated with tanning oil substantially permanently attached to the inner surface of a flexible impermeable backing member 14d. The backing member and carrier pad have an hourglass-shaped configuration which is substantially symmetrical with respect to a central fold line 42 so that substantially identically shaped fold portions 44a and 44b are provided on opposite sides of fold line 42. Adhesive 26d is provided on the peripheral region 16d of backing member 14d.

In assembly of the closed combination package and applicator 10d, outer fold lines 46a and 46b are preliminarily formed in respective fold portions 44a and 44b, fold lines 46a and 46b extending substantially parallel to the central fold line 42. The backing member and carrier pad are folded at line 42 as seen in FIG. 9 and the opposed portions of the peripheral region 16d sealed to each other by adhesive 26d to seal the carrier pad 12d in the enclosed space formed between the backing member fold portions 44a and 44b.

In use, the opposed fold portions 44a and 44b are peeled away from each other to expose the outer parts of pad 12d until the outer fold lines 46a and 46b are reached. The opposed regions of central portion 48 of the backing member situated inwardly of outer fold lines 46a and 46b and which remain sealed to each other function as a handle 20d to be grasped as seen in FIG. 10 during the application of the tanning oil to the body. As is readily apparent, the oil can be applied without the fingers coming into contact with the tanning oil during application.

The combination package and applicator of the present invention is extremely convenient in use eliminating the necessity for the user to carry a bottle or tube containing the substance with him. When used as an applicator, the user's hand will not come into contact with the substance being applied to the body or to other articles. The combination package and applicator is disposable after a single use.

Obviously, numerous modifications and variations of the present invention are possible in the light of the above teachings. It is therefore to be understood that within the scope of the claims appended hereto, the invention may be practiced otherwise than as specifically disclosed herewith.

What is claimed is:

1. A combination package and applicator for moist and/or greasy substances, comprising:
   a flexible backing member formed of a material that is impermeable to moisture and grease;
   a carrier impregnated with said substance substantially permanently affixed to a surface of said backing member;
   said carrier being sealed within an enclosed space defined at least in part by said backing member when said combination package and applicator is closed; and
   grasping means associated with said backing member by which said combination package and applicator can be firmly gripped by the user and the substance applied without coming into contact with said substance impregnated carrier;
   wherein said grasping means comprise said backing member formed by a pair of opposed sheet portions; and
   wherein said opposed sheet portions are connected to each other along peripheral side regions to define an open end into which at least several fingers of a user's hand can be insterted.

2. The combination of claim 1 wherein said carrier comprises a fibrous pad formed of absorbent material.

3. The combination of claim 1 wherein said backing member is formed of a sheet of metallic foil.

4. The combination of claim 1 wherein said backing member is formed of a sheet of suitably prepared paper.

5. The combination of claim 1 wherein said enclosed space in which said carrier is sealed is formed by a cover sheet formed of impermeable material, said cover sheet and backing sheet having opposed peripheral edge regions which are sealed to each other.

6. The combination of claim 1, wherein said opposed sheet portions form a mitt-like member into which the user's hand can be inserted.

7. The combination of claim 1, wherein said backing member is folded over itself at a fold line to define said opposed sheet portions which are glued to each other along said peripheral side regions, one of said glued peripheral side regions being opposite said open end.

8. The combination of claim 5, wherein said cover sheet is sealed to one of said opposed sheet portions of said backing sheet.

9. The combination of claim 8, wherein said cover sheet is substantially flat and extends over substantially said entire sheet portion of said backing sheet.

* * * * *